United States Patent [19]

Runeman et al.

[11] Patent Number: 5,401,266
[45] Date of Patent: Mar. 28, 1995

[54] ABSORBENT ARTICLE

[75] Inventors: Bo Runeman, Partille; Peter Rönnberg, Mölndal, both of Sweden

[73] Assignee: Molnlycke AB, Gothenburg, Sweden

[21] Appl. No.: 856,914

[22] PCT Filed: Nov. 16, 1990

[86] PCT No.: PCT/SE90/00743

§ 371 Date: Jun. 22, 1992

§ 102(e) Date: Jun. 22, 1992

[87] PCT Pub. No.: WO91/07156

PCT Pub. Date: May 30, 1991

[30] Foreign Application Priority Data

Nov. 17, 1989 [SE] Sweden ............................ 8903869

[51] Int. Cl.⁶ ...................... A61F 13/15; A61F 13/20
[52] U.S. Cl. ...................... 604/378; 604/358; 604/373; 604/381; 604/382; 604/383; 604/385.1; 604/385.2
[58] Field of Search ............ 604/358, 385.1, 385.2, 604/366, 369, 370, 372, 373, 378, 381–383

[56] References Cited

U.S. PATENT DOCUMENTS

| 2,928,389 | 3/1960 | Ganz et al. | 604/378 |
| 3,881,489 | 5/1975 | Hartwell | 604/372 |
| 3,882,871 | 5/1975 | Taniguchi | 604/385.2 |
| 3,888,248 | 6/1975 | Moore et al. | 604/370 |
| 3,901,240 | 8/1975 | Hoey . | |
| 4,000,028 | 12/1976 | Hoey . | |
| 4,036,234 | 7/1977 | Ishizuka | 604/378 |
| 4,074,721 | 2/1978 | Smits et al. | 604/370 |
| 4,306,559 | 12/1981 | Nishizawa et al. | 604/371 |
| 4,341,216 | 7/1982 | Obenour | 604/370 |
| 4,548,604 | 10/1985 | Ellsworth | 604/385.2 |
| 4,938,756 | 7/1990 | Salek | 604/368 |
| 5,019,069 | 5/1991 | Klemp | 604/387 |
| 5,037,417 | 8/1991 | Ternström et al. | 604/385.2 |
| 5,133,705 | 7/1992 | Nakanishi et al. | 604/389 |

FOREIGN PATENT DOCUMENTS

| 0238334 | 9/1987 | European Pat. Off. . |
| 0406035 | 1/1979 | Sweden . |
| 412881 | 3/1980 | Sweden . |
| 2107991 | 5/1983 | United Kingdom . |

Primary Examiner—Randall L. Green
Assistant Examiner—P. Zuttarelli
Attorney, Agent, or Firm—Young & Thompson

[57] ABSTRACT

An absorbent article intended for use as a urine-collecting insert in a diaper or an incontinence guard includes an inner casing layer (2) of liquid permeable material, which when the article is worn lies nearest the body of the wearer, an outer liquid permeable casing layer (3) and an absorbent pad (4) located between the casing layers. The outer casing layer (3) has a lower liquid permeability than the inner casing layer (2), such that liquid absorbed by the article is able to pass through the outer casing layer and absorbed by the diaper or incontinence guard, relatively slowly and in a controlled fashion.

8 Claims, 3 Drawing Sheets

ABSORBENT ARTICLE

FIELD OF THE INVENTION

The present invention relates to an absorbent article intended for use as a urine-collecting insert in a disposable diaper or an incontinence guard, said article including an inner casing layer of liquid permeable material which lies nearest the body of the wearer in use, an outer liquid permeable casing layer, and an absorbent body or pad enclosed between said casing layers.

BACKGROUND OF THE INVENTION

An adult incontinence guard must be adapted to the type of incontinence for which it is to provide a guard. In milder forms of incontinence where only small quantities of fluid are discharged, a thin, small guard may suffice to protect the underwear of the wearer, whereas heavier incontinence will require diapers of high absorption capacity and leakage reliability. Furthermore, for anatomical reasons, male and female incontinence guards must be configured differently. The specific problems encountered when configuring male incontinence guards reside primarily in the tendency of the male penis to move readily in the guard, or to be positioned incorrectly when putting on the guard. Consequently, in the case of known male incontinence guards, it is impossible to anticipate that region of the guard in which wetting will primarily occur. In the case of female incontinence guards, on the other hand, a so-called wetting point can be determined more readily, and, consequently, it is easier to optimize the absorption capacity of female incontinence guards.

Leakage will often occur in known male incontinence guards because urine has either been delivered to one side of the guard or to random regions thereof. Because the urine has been absorbed within random regions of the incontinence guard, parts of the absorption material will have become saturated with liquid, resulting in leakage, whereas other parts of the absorption material will have remained unused.

SUMMARY OF THE INVENTION

As a result of the present invention, there is provided an article of the kind mentioned in the introduction which reduces the risk of leakage when large quantities of urine are discharged. The inventive article is primarily characterized in that the outer casing layer has a lower liquid permeability than the inner casing layer, and, consequently, liquid absorbed in the article is able to pass to the outer casing layer in a relatively slow and controlled fashion, and collect in the diaper or incontinence guard.

The inventive article can be used by both men and women, and therewith solves the particular problems mentioned above and associated with the use of male diapers or incontinence guards.

When the inventive article is used by men, the article is placed over the genitals of the wearer. A conventional, adult diaper is normally placed externally of the article, with respect to the wearer. The article receives all urine that is discharged, said urine being transferred progressively to the externally located diaper as the absorbent pad of the article becomes saturated. The diaper is thus able to slowly absorb the liquid transported from the article.

According to one embodiment of the invention, the outer casing layer of the article is divided into zones of mutually different degrees of liquid permeability. This affords the possibility of guiding the liquid absorbed by the article to selected parts of the diaper which exhibit particularly high absorption capacities or liquid dispersion ability, besides affording an additional guard against limited regions of the diaper becoming quickly saturated with liquid and therewith causing leakage.

BRIEF DESCRIPTION OF THE DRAWINGS

The invention will now be described in more detail with reference to an exemplifying embodiment thereof illustrated in the accompanying drawings, in which FIG. 2 is a perspective view of the article illustrated in FIG. 1 with the elastication active; while

DETAILED DESCRIPTION OF THE INVENTION

Figure 1:
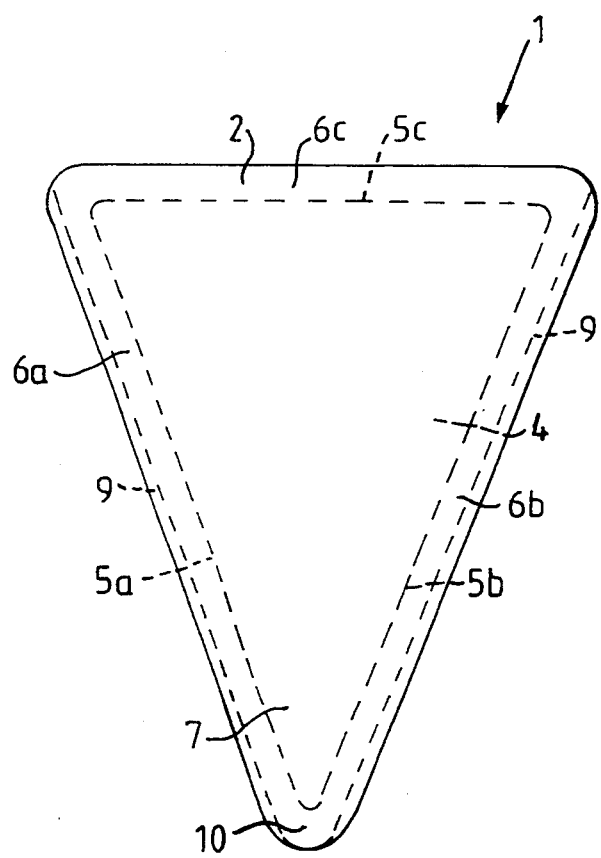
FIG. 1 illustrates one embodiment of an inventive article in a stretched or extended state, with the side intended to lie against the wearer in use facing towards the viewer.
Figure 2:
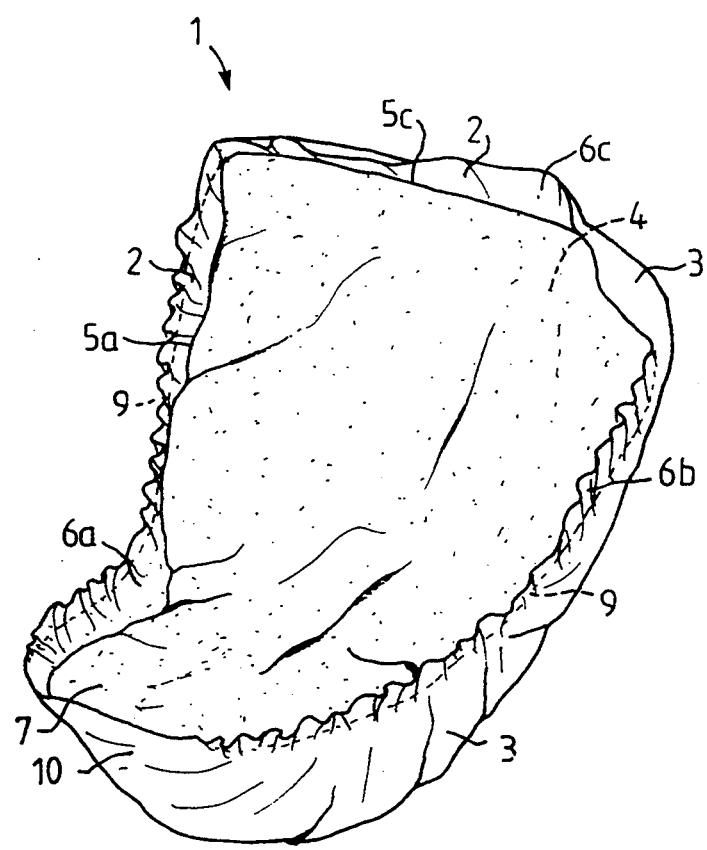

The article 1 illustrated in FIGS. 1–2 comprises an inner liquid-permeable casing layer 2, an outer casing layer 3 and an absorption body or pad 4 enclosed between the two layers 2 and 3.

The absorbent pad 4 may comprise an absorbent fibre material, such as fluff. If desired, this material can be mixed with another absorbent material, for instance so-called superabsorbent polymers, by which is meant polymers that are able to absorb liquid in quantities equivalent to many times the natural weight of the polymers. Non-absorbent substances, such as melt fibres, can also be admixed with the absorbent pad. The pad may include either a single absorbent layer or two or more absorbent layers having mutually different material compositions. Differences with respect to the type of material and the length of material used may also occur within one and the same layer and between different parts thereof. The absorbent pad 4 has the configuration of an isosceles triangle, having two equally long side edges 5a and 5b and a third shorter side edge 5c.

The inner liquid permeable casing layer 2 will preferably consist of non-woven fibre fabric. Another conceivable material is perforated plastic. The outer casing layer 3 has a lower liquid permeability than the inner casing layer 2. This can be achieved by forming the outer casing layer 3 from a perforated plastic or a hydrophofically-treated fibre fabric. Parts of the outer casing layer may consist of a liquid-impervious material, for instance plastic, while other parts can consist of the aforesaid, more liquid-permeable materials. The casing layers 2 and 3 are preferably of the same size and shape, and beth of said layers extend slightly beyond the edges 5a, 5b, 5c of the absorbent pad, such as to form side flaps 6a, 6b, 6c along which the casing layers 2 and 3 are mutually joined by means of a binder, such as melt glue. The equally long edges 5a, 5b of the absorbent pad are therewith corresponded by side flaps 6a, 6b of mutually equal length, and the third edge 5c of the absorbent pad is corresponded by a third side flap 6c. The elastic devices 9 extend from the pointed end 10 along each of the side edges (5a, 5b) of the absorbent pad over at least part of the length of the side edges.

The article 1 constitutes a complement to a traditional diaper and is intended to be placed nearest the body of the wearer over the male organs, whereafter a diaper (not shown) of any chosen kind is placed externally on the article 1.

Because the article is placed over the genital organs of the wearer, the article will take-up the first of the urine discharged, often in large quantities. When the article has become saturated, liquid will slowly pass through the outer casing layer 3 and be subsequently absorbed by the outwardly lying diaper. This enables the diaper, in turn, to slowly absorb the liquid, without risk of leakage past the diaper edges, as would otherwise be the case, owing to the fact that a diaper does not normally have time to accommodate large quantities of liquid that are discharged at one and the same time. The article thus retards the flow of liquid while ensuring that liquid will not be delivered to diaper regions other than those which lie against the article, in any other way other than through absorption dispersion in the diaper.

Elastic devices 9 are embodied in the side flaps 6a, 6b of mutually equal lengths while in a stretched state. The elastic devices 9, for instance, may have the form of elastic threads, bands or the like. The use of elastic foam material is also conceivable in this regard. The elastic devices are suitably glued to one or to both of the casing layers. The elastic devices may be placed at any desired distance from the edges 5a, 5b of the absorbent pad and from the side flaps 6a, 6b, 6c. A curved, container-like part 7 is obtained at the pointed end 10 of the article located between the two side flaps of mutually equal lengths. The pointed end 10 is intended to be placed beneath the scrotum of a male wearer when the article is in use. The curvature of the article and the formation of the container-like part 7 is achieved due to the fact that the elastic devices 9, which are located in the side flaps 6a, 6b along the two converging edges 5a, 5b of the absorbent pad 4 contract from a pretensioned state. Because the absorbent pad narrows in a direction towards said pointed end 10, its local resistance to bending around transverse axes decreases in conformity with this narrowing of the pad. Thus, the absorbent pad 4 is curved more pronouncedly at locations nearest the pointed end 10 than in other pad parts, as will be seen from FIG. 2 which shows the article subsequent to contraction of the elastic devices.

The elastic bias may have different or equal values within different parts of the side flaps 6a, 6b. Naturally, it is conceivable to introduce different degrees of elastic bias or pre-tension, depending on the desired curvature and desired size of the object.

According to one preferred embodiment of the invention, the elastic devices are attached in the side flaps 6a, 6b in spaced relationship with the edges 5a, 5b of the absorbent pad. The elastic devices 9 will therewith raise the side flaps 6a, 6b, so as to form leakage-preventing barriers. Furthermore, the side flaps 6a, 6b can be utilized readily and in a practical manner when the article is used by men. Thus, the article is first twisted so that it will curve in a direction opposite to that intended when using the article, whereafter the pointed end 10 of the article is gripped by the fingers of one hand in the vicinity of a region of the side flaps 6a, 6b between the elastic devices 9 and the edges 5a, 5b of the absorbent pad, whereafter the article is passed over the male organs of the wearer and twisted into position, with the aid of the elastication. The elastic devices also have a retaining action and counteract sideward movement of the article when worn, which renders the article particularly suitable for use as an insert in an incontinence guard or a diaper.

The elastic devices can also be applied over the absorbent pad, although in this case the elastic devices will not cause the side flaps 6a, 6b to lift and form leakage barriers.

Figure 3:
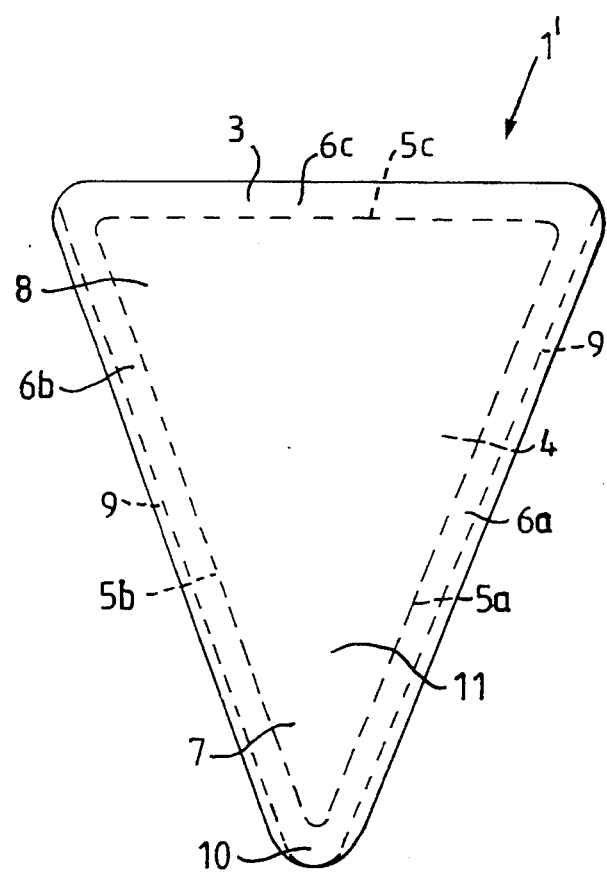
FIG. 3 illustrates a second embodiment of an inventive article in an extended or stretched state, with the side intended to lie against the wearer in use facing away from the viewer.

FIG. 3 illustrates an article 1' which identical to the article illustrated in FIGS. 1-2, with the exception that the outer casing layer 3 is divided into an upper and a lower zone, referenced 8 and 11 respectively.

The remaining parts of the article 1' are identified with the same reference signs as those used to identify corresponding parts of the incontinence guard 1 illustrated in FIGS. 1-2.

The upper zone 8 extends from outer edges of that side flap which, when the article 1' is worn, is intended to be turned up against the stomach of the wearer, and extends parallel with the side flap 6c, approximately half way towards the pointed end 10. The outer casing layer is liquid permeable in the upper zone 8 and comprises, for instance, a perforated plastic material or a hydrophofically-treated non-woven material.

The lower zone 11 includes that part of the outer casing layer which continues from the upper zone 8 down to the pointed end 10. The lower zone 11 comprises, for instance, a liquid impermeable material, for instance polyethelene plastic.

The degree of liquid-permeability of the various zones, and also the number and location of said zones, can be varied endlessly. For instance, in the case of the embodiment illustrated in FIG. 3, both the upper and the lower zones 8, 11 may consist of a liquid permeable material in the form of perforated plastic or the like, in which the number of perforations and/or the size of said perforations differ from one zone to the other. It is also conceivable to impart solely to the side flaps 6a, 6b, 6c and a region of the outer casing layer located immediately inwardly of the side flaps a liquid permeability which is lower than the remaining triangular region thus obtained in the centre of the outer casing layer.

The invention shall not be considered to be limited to the aforedescribed exemplifying embodiments thereof, since several modifications can be made within the scope of the following claims.

The article has an essentially triangular shape. Various triangular shapes are conceivable within the scope of the invention, such as the shape of an isosceles triangle, equilateral triangle or a scalene triangle. Furthermore, the triangular shapes may have rounded corners, and triangular shapes with non-linear edges are also conceivable. With the intention of enabling the article to be gripped more readily when putting-on said article, in the aforedescribed manner, rounded recesses may advantageously be formed in the absorbent pad. This will also provide higher leakage barriers, since the distance between the flap edges and the pad edges increase as a result of these recesses.

It is also conceivable to incorporate some form of absorbent material in the side flaps. In order to obtain a good elastic seal and enable the article to be twisted readily when putting on said article, it is necessary for the material in the side flaps to be more flexible and bendable than the material in the absorbent pad.

In the aforegoing, the article has been described as being particularly suitable for men. The article, however, can be used advantageously also by women, as an insert in diapers or incontinence guards. It can also be used advantageously with children's diapers.

The article can be symmetrically configured, so as to form a basin-like space between respective corners, this configuration being particularly suitable for women.

The invention is not restricted to elasticated articles, but can be applied as a non-elasticated urine-collecting insert and in any suitable form whatsoever.

We claim:

1. A urine-collecting insert for a diaper or an incontinence guard, said insert being sized and configured to be placed over the genital organs of a wearer and comprising a liquid permeable facing which is intended to lie closest to the wearer's body in use and comprises an inner casing layer of liquid permeable material, a liquid permeable backing consisting of a liquid permeable outer casing layer, said inner casing and outer casing layers having lateral edges and being mutually joined at said edges, and an absorbent pad interposed between said facing and backing and in direct contact with said outer casing layer in a central area of said pad, said backing having a lower liquid permeability than said facing and allowing liquid transfer from said absorbent pad through said backing progressively as the absorbent pad becomes saturated, thereby enabling liquid absorbed by the insert to spread in said absorbent pad and pass through the backing relatively slowly and in a controlled fashion.

2. An insert according to claim 1, wherein the outer casing layer consists of a perforated liquid-impervious material.

3. An insert according to claim 1, wherein the outer casing layer consists of a liquid permeable material.

4. An insert according to claim 3, wherein the outer casing layer consists of a hydrophobically-treated liquid permeable material.

5. An insert according to claim 1, wherein the outer casing layer presents zones which exhibit mutually different degrees of liquid permeability, therewith enabling transportation of liquid through the outer casing layer to be guided and controlled.

6. An insert according to claim 5, wherein the mutually different degrees of liquid permeability of said zones is achieved through mutually different degrees of perforation or mutually different degrees of hydrophobicity.

7. An insert according to claim 1, wherein the absorbent pad, at least in a first part thereof intended, in use, to embrace a wearer's crotch either completely or partially, narrows towards a free end of said first part; at least one elastic device being attached, in a pretensioned state, to the inner casing layer and extending from the free end along side edges of the absorbent pad over at least a portion of said side edges; and wherein contraction of said at least one elastic device from its pretensioned state causes said first part of the absorbent pad to take a curved shape so that when the article is worn, said first part will be curved inwardly beneath the crotch of the wearer.

8. An insert according to claim 7, wherein the outer casing layer includes an upper zone which has at least an extension, said extension, when the insert is worn, being intended to be turned up towards a wearer's stomach, and a lower zone which extends from the upper zone to the free end of the insert; and said upper zone being more permeable to liquid than the lower zone.

* * * * *